(12) United States Patent
Trembly

(10) Patent No.: US 7,377,917 B2
(45) Date of Patent: May 27, 2008

(54) FEEDBACK CONTROL OF THERMOKERATOPLASTY TREATMENTS

(75) Inventor: B. Stuart Trembly, Hanover, NH (US)

(73) Assignee: The Trustees of Dartmouth College, Hanover, NH (US)

( * ) Notice: Subject to any disclaimer, the term of this patent is extended or adjusted under 35 U.S.C. 154(b) by 152 days.

(21) Appl. No.: 10/314,670

(22) Filed: Dec. 9, 2002

(65) Prior Publication Data

US 2004/0111086 A1    Jun. 10, 2004

(51) Int. Cl.
*A61B 18/18* (2006.01)

(52) U.S. Cl. .......................... 606/32; 606/34; 606/41; 607/96; 607/101

(58) Field of Classification Search ................ 606/4–6, 606/10, 27–34, 41, 42, 50; 607/96–101
See application file for complete search history.

(56) References Cited

U.S. PATENT DOCUMENTS

| | | | |
|---|---|---|---|
| 603,815 A | 5/1898 | Duke | |
| 1,108,686 A | 8/1914 | Bonis | |
| 1,364,148 A | 1/1921 | Springer | |
| 2,126,070 A | 8/1938 | Wappler | |
| 2,347,915 A | 5/1944 | Landaüer | |
| 2,525,381 A | 10/1950 | Tower | |
| 3,237,623 A | 3/1966 | Gordon | |
| 3,307,533 A | 3/1967 | Meredith et al. | |
| 3,948,269 A | 4/1976 | Zimmer | |
| 3,978,864 A | 9/1976 | Smith et al. | |
| 3,991,770 A | 11/1976 | LeVeen | |
| 4,003,383 A | 1/1977 | Bruck | |
| 4,014,333 A | 3/1977 | McIntyre | |
| 4,030,480 A | 6/1977 | Meyer | |
| 4,140,130 A | 2/1979 | Storm, III | |
| 4,326,529 A | 4/1982 | Doss et al. | |
| 4,381,007 A | 4/1983 | Doss | |
| 4,528,991 A | 7/1985 | Dittmar et al. | |
| 4,881,543 A | 11/1989 | Trembly et al. | |
| 5,263,951 A * | 11/1993 | Spears et al. | 606/12 |
| 5,368,590 A * | 11/1994 | Itoh | 606/4 |
| 5,437,658 A * | 8/1995 | Muller et al. | 606/5 |
| 5,458,596 A | 10/1995 | Lax et al. | |

(Continued)

FOREIGN PATENT DOCUMENTS

EP    0 422 112 B1    7/1996

OTHER PUBLICATIONS

Trembly, B.S.; Hashizume, N.; and Moodie, K.S.: "Microwave Thermal Keratoplasty For Myopia: Keratoscopic Evaluation In Porcine Eyes" Journal Of Refractive Surgery, 2001, pp. 682-688.

(Continued)

*Primary Examiner*—A. Farah
(74) *Attorney, Agent, or Firm*—Lathrop & Gage

(57) ABSTRACT

A microwave thermokeratoplasty system uses an applicator having embedded sensors that provide feedback signals to a controller. The controller interprets these feedback signals to dynamically adjust or cease a keratoplasty operation. The system uses a microwave applicator that is specially adapted for direct application of energy to an eye in the course of treatment. The applicator is formed of discrete zones or sectors that are selectively controlled in an individual manner.

23 Claims, 4 Drawing Sheets

U.S. PATENT DOCUMENTS

| | | | |
|---|---|---|---|
| 5,749,871 A | 5/1998 | Hood et al. | |
| 5,779,696 A * | 7/1998 | Berry et al. | 606/16 |
| 5,948,011 A | 9/1999 | Knowlton | |
| 6,024,095 A * | 2/2000 | Stanley, III | 128/898 |
| 6,053,909 A | 4/2000 | Shadduck | |
| 6,149,620 A | 11/2000 | Baker et al. | |
| 6,149,643 A | 11/2000 | Herekar et al. | |
| 6,159,205 A | 12/2000 | Herekar et al. | |
| 6,224,593 B1 | 5/2001 | Ryan et al. | |
| 6,364,875 B1 * | 4/2002 | Stanley, III | 606/27 |
| 6,413,255 B1 | 7/2002 | Stern | |
| 6,461,354 B1 | 10/2002 | Olsen et al. | |
| 6,482,201 B1 | 11/2002 | Olsen et al. | |
| 6,491,688 B1 | 12/2002 | Lin et al. | |
| 6,520,956 B1 | 2/2003 | Huang | |
| 6,623,454 B1 | 9/2003 | Eggers et al. | |
| 6,673,069 B1 | 1/2004 | Hood | |
| 6,773,431 B2 | 8/2004 | Eggers et al. | |
| 6,890,332 B2 | 5/2005 | Truckai et al. | |
| 6,939,344 B2 | 9/2005 | Kreindel | |
| 7,044,945 B2 * | 5/2006 | Sand | 606/12 |
| 7,192,429 B2 * | 3/2007 | Trembly | 606/41 |
| 2002/0002369 A1 | 1/2002 | Hood | |
| 2002/0042612 A1 | 4/2002 | Hood et al. | |
| 2002/0099363 A1 | 7/2002 | Woodward et al. | |
| 2002/0143322 A1 | 10/2002 | Haghighi | |
| 2002/0173777 A1 | 11/2002 | Sand | |
| 2003/0028228 A1 | 2/2003 | Sand | |
| 2003/0163178 A1 | 8/2003 | Davison et al. | |
| 2003/0174281 A1 | 9/2003 | Herekar et al. | |
| 2003/0181899 A1 | 9/2003 | Hood et al. | |
| 2003/0181903 A1 | 9/2003 | Hood et al. | |
| 2007/0161976 A1 | 7/2007 | Trembly | |

OTHER PUBLICATIONS

Office Action dated Mar. 28, 2006 issued in related U.S. Appl. No. 10/730,327.
Response to Office Action dated Mar. 28, 2006 in related U.S. Appl. No. 10/730,327 filed on Aug. 28, 2006.
Notice of Allowance dated Nov. 14, 2006 issued in related U.S. Appl. No. 10/730,372.
Office Action dated Aug. 24, 2007 issued in related U.S. Appl. No. 11/688,146.
International Search Report dated Jun. 11, 2004, issued in related PCT Patent Application PCT/US2003/38978.
International Preliminary Examination Report dated Mar. 22, 2005, issued in related PCT/ Patent Application PCT/US2003/38978.
Rule 109 and 110 Notice dated Aug. 5, 2005, issued in related Eurpoean Patent Application 03796799.
Response to Rule 109 and 110 Notice dated Aug. 5, 2005, in related European Patent Apllication 03796799 filed on Sep. 9, 2005.

* cited by examiner

FEEDBACK CONTROL OF THERMOKERATOPLASTY TREATMENTS

BACKGROUND

1. Field of the Invention

The invention pertains to the field of keratoplasty and, more particularly, to thermokeratoplasty, especially electrically-induced thermokeratoplasty such as radio frequency or microwave thermokeratoplasty.

2. Description of the Related Art

The object of keratoplasty is to correct vision by reshaping of the cornea. For nearsighted persons, this reshaping involves flattening that ideally decreases the refractive power of the eye and causes the image to focus upon the retina, as opposed to focusing images in front of the retina. Invasive surgical procedures, such as laser-assisted in-situ keratonomileusis (LASIK) may be used, but there are associated complications, such as the dry eye syndrome associated with severing of corneal nerves, and the need for a healing period after surgery.

Thermokeratoplasty is a noninvasive procedure that may be used to correct the vision of near sighted persons by flattening the cornea. Generally, the cornea is heated to a point where collagen fibers in the cornea shrink, which results in stresses that tend to reshape the cornea. Thermokeratoplasty may be performed by the use or absorption of electrical energy, which is typically cycled in the microwave or radio frequency band for this purpose. Microwave thermokeratoplasty uses a near field microwave applicator to apply energy to the cornea, raising the corneal temperature. At about 60° C., the collagen fibers in the cornea shrink, and the onset of shrinkage is sudden. Resultant stresses from this shrinkage reshape the corneal surface. Application of energy in this manner may cause reshaping that flattens the central cornea when the energy is applied in circular or ring-shaped patterns around the pupil.

Devices and methodologies for microwave thermokeratoplasty are shown and described in U.S. Pat. No. 4,881,543 to Trembly et al., which is hereby incorporated by reference to the same extent as though fully replicated herein. The microwave applicator comprises an open-ended coaxial antenna driven at 915 MHz or 2540 MHz with an internal coolant system that drives flow of saline coolant transverse to the antenna axis. The '543 patent advances the art by providing applied electrical field theory for open-ended coaxial applicators and the related specific absorption rate, e.g., by using the Swicord and Davis technique in addition to heat transfer theory involving the Nusselt number, the Reynolds Number, and the dimensions of the gap between the antenna and the cornea.

Generally, these devices and methodologies are referred to as "microwave thermokeratoplasty" even though emissions at 915 MHz are slightly below the 1 GHz cutoff that many persons use to identify the microwave band. The term "radio frequency thermokeratonomy" may be used to describe energetic keratoplasty by excitation at lower frequencies. Microwave and radio frequency thermokeratoplasty may be used to achieve similar results, but the applied energy affects the tissue in different ways according to the various theories of operation where the radio frequency heating of tissue has a larger resistive heating component.

FIG. 1 is a side midsectional view illustrating a conventional microwave applicator 100 deployed for use in microwave thermokeratoplasty operations on a cornea 102. An oscillator drives microwave field emissions on concentric microwave conductors, such as conductive metal tubes 104 and 106. A dielectric 108 fills space between the tubes 104 and 106. A central passageway 110 permits the flow of coolant 112 into a flow gap 114 of about 0.3 mm to 0.5 mm between a terminal antenna end 116 and a Mylar™ (a trademark of E. I. du Pont de Nemours and Company Corporation, of Wilmington, Del.) film 118. The flow gap 114 places the central passageway 110 in fluidic communication with exit annulus 120 for circulation of coolant 112. The Mylar™ film 118 comes into direct contact with cornea 102 at interface 122, which may optionally have a concave down configuration adapted so as not to over-stress the cornea 102 by excessive flattening.

As shown in FIG. 1, the configuration of applicator 100 provides a microwave field that distributes itself downward through the coolant in flow gap 114 and into the cornea 102. The tubes 104 and 106 form an inefficient near-field applicator ideally having a penetration depth of less than about one millimeter, as opposed to a true antenna that can launch a wave. The small value of microwave penetration depth is an intentional design feature that is intended to protect the endothelium or back surface 124 of cornea 102 because the endothelium 124 is regarded to be incapable of regeneration after thermal damage. Coolant 112 flowing in the flow gap 114 cools the cornea at interface 122 by forced convection. The Mylar™ film 118 retains the coolant 112 in flow gap 114 and also prevents the flow of electrical current from tubes 104 and 106 into the cornea 102. By balancing the heating effects of applied microwave field against the cooling benefits of coolant 112, a local maximum of temperature is produced at near mid-depth of the cornea 102 while protecting the corneal epithelium (front surface) and the endothelium 124 (rear surface) from thermal damage.

A number of problems have arisen in use of prior microwave applicator devices. Chiefly, the amount of applied energy is unpredictably related in terms of a precise biological effect, such as by administering energy to produce a predetermined amount of vision correction. The thermal flux at depth in the cornea can be calculated according to theory with a high degree of precision; however, the thermal flux is not calibrated to a measurable biological effect in terms of an applied treatment modality. For example, it is undetermined what level of thermal flux is required to flatten a particular cornea to a desired level of diopter adjustment. This uncertainty is exacerbated by the characteristically sudden onset of thermally-induced shrinkage in the cornea. There is no clear way to determine in the course of treatment if, for example, the outermost layer of corneal cells known as the epithelium is undergoing thermal damage as a result of treatment, and this uncertainty can lead to a painful period of healing while the epithelium regenerates. Critical, small dimensions in the applicators may vary with machining errors, assembly or use, most notably in the dimensions of flow gap 114 for the coolant. Even small machining errors in these dimensions result in the applicator producing asymmetric treatment rings and associated astigmatic effects on the "corrected" vision resulting from use of these devices.

There is a need to improve the predictability of effectiveness of microwave thermokeratoplasty applicators and to reduce the unintended harm that such devices may produce.

SUMMARY OF THE INVENTION

The present invention overcomes the problems outlined above and advances the art by providing a microwave application device and system that is less likely to produce unintended harm, such as astigmatic effects and burning of epithelial or endothelial corneal tissues. The device and system is advantageously configurable for use in treatment modalities that are predictable or verifiable in their effects upon vision correction.

The thermokeratoplasty system may include an energy transmitter used for cornea-based vision correction modalities. According to the various instrumentalities and embodiments of this system, an improvement to prior systems may comprise a sensor that is configured to measure a physical variable in an eye as the eye is affected by a thermokeratoplasty operation and to provide a sensor signal representative of the physical variable. A feedback circuit may be adapted to receive the sensor signal and analyze the sensor signal to determine when a treatment modality has achieved an intended effect.

By way of example, the sensor may be configured to measure the physical variable as corneal temperature, either as a surface temperature or temperature at depth in the cornea. The sensor may also or alternatively be configured to measure the physical variable as heat flux in the cornea, mechanical stress of the cornea, mechanical strain of the cornea or an electrical property of the cornea, such as the phenomenon of conductivity or permittivity. The sensor may be configured to measure the physical variable as a mechanical property of the cornea, for example, mass density, modulus of elasticity, or a change in optical opacity associated with shrinkage of collagen in the cornea.

The sensor signal may derive from many forms of measurement. For example the sensor signal may embody information concerning a quantity of electrical current passing through the cornea, an electrical voltage applied to the cornea, and/or electromagnetic energy applied to the cornea, such as reflected energy, transmitted energy, and energy received from tissue. The electromagnetic energy may be measured as an optical birefringence phenomenon and/or a microwave radiometry phenomenon. Ultrasonic energy may also be applied to the cornea for use in measurements, for example, as measurements of reflected energy, transmitted energy, and/or energy received from tissue.

The sensor signal may embody information obtained from a mechanical transducer, such as a piezo-resistive or piezoelectric device that is oriented to quantify parameters including corneal elongation, corneal compression, corneal displacement, corneal velocity, corneal acceleration, local slope, local curvature, global slope, global curvature, corneal stress, or corneal pressure. These measurements may pertain to scalar, vector, or tensor variables measured at the surface of the cornea or at depth in the cornea. Alternatively, a thermal transducer may be used to determine, for example, temperature and heat flux at the surface of the cornea or at depth in the cornea. Useful types of thermal transducers may include, without limitation, a thermocouple, a thermistor, and a submillimeter-scale device.

The feedback circuitry may operate by using signals and signal processing circuits, such as by processing a sensor signal according to an empirical correlation that relates the sensor signal to a predetermined vision correction effect. The feedback circuitry may also operate by processing the sensor signal to determine when the physical variable has been adjusted to achieve a predetermined quantity of the physical variable, such as a predetermined level of birefringence.

According to various instrumentalities and embodiments herein, at least one additional sensor may be used to provide an additional sensor signal. The feedback circuitry may be configured to process the sensor signals in combination to determine when the treatment modality has achieved the intended effect as a function of the respective signals.

In one embodiment, the microwave or radio frequency applicator is configured for direct contact with the cornea without a coolant flow gap between the microwave or radio frequency applicator and the cornea. The microwave applicator may include a plurality of discrete sectors that are optionally actuated by control circuitry in a selective and independent manner for the emission of microwave or radio frequency energy according to the treatment modality. Program instructions for the control circuitry may, for example, provide a capability to change the actuation of one or more of the plurality of discrete sectors on the basis of the sensor signal. To compliment this functionality, the sensor may include an array of sensors each allocated to a corresponding one of the plurality of discrete sectors and linked to the feedback circuitry.

Other instrumentalities involve special features of a radio frequency or microwave thermokeratoplasty applicator. A plurality of concentric tubes each may have a top end and a bottom surface configured to apply electrical energy for keratoplasty operations. A dielectric material may separate the plurality of concentric tubes from one another. A cooling system may be configured to cool the applicator during keratoplasty operations without flowing coolant beneath the bottom surface 116. This type of cooling system eliminates systematic errors that are introduced by virtue of having a flow gap of varying dimensions, e.g., flow gap 114 (shown in FIG. 1). For example, the cooling system may comprise a Peltier effect or thermoelectric cooling device or a system for circulating liquid coolant in upper regions of the applicator, but not bottom regions proximate the bottom surface of the applicator. A vacuum positioning system may optionally be used to retain the applicator on a cornea.

In use, the thermokeratoplasty system facilitates a thermokeratoplasty modality that employs an energy transmitter used for cornea-based vision correction modalities. The method of operation may, for example, include applying microwave or radiofrequency energy or other heat transmitting energy, sensing a physical variable in an eye as the eye is affected by a thermokeratoplasty operation to provide a sensor signal representative of the physical variable, receiving the sensor signal, and analyzing the sensor signal to determine when a treatment modality has achieved an intended effect.

DETAILED DESCRIPTION

Figure 2:
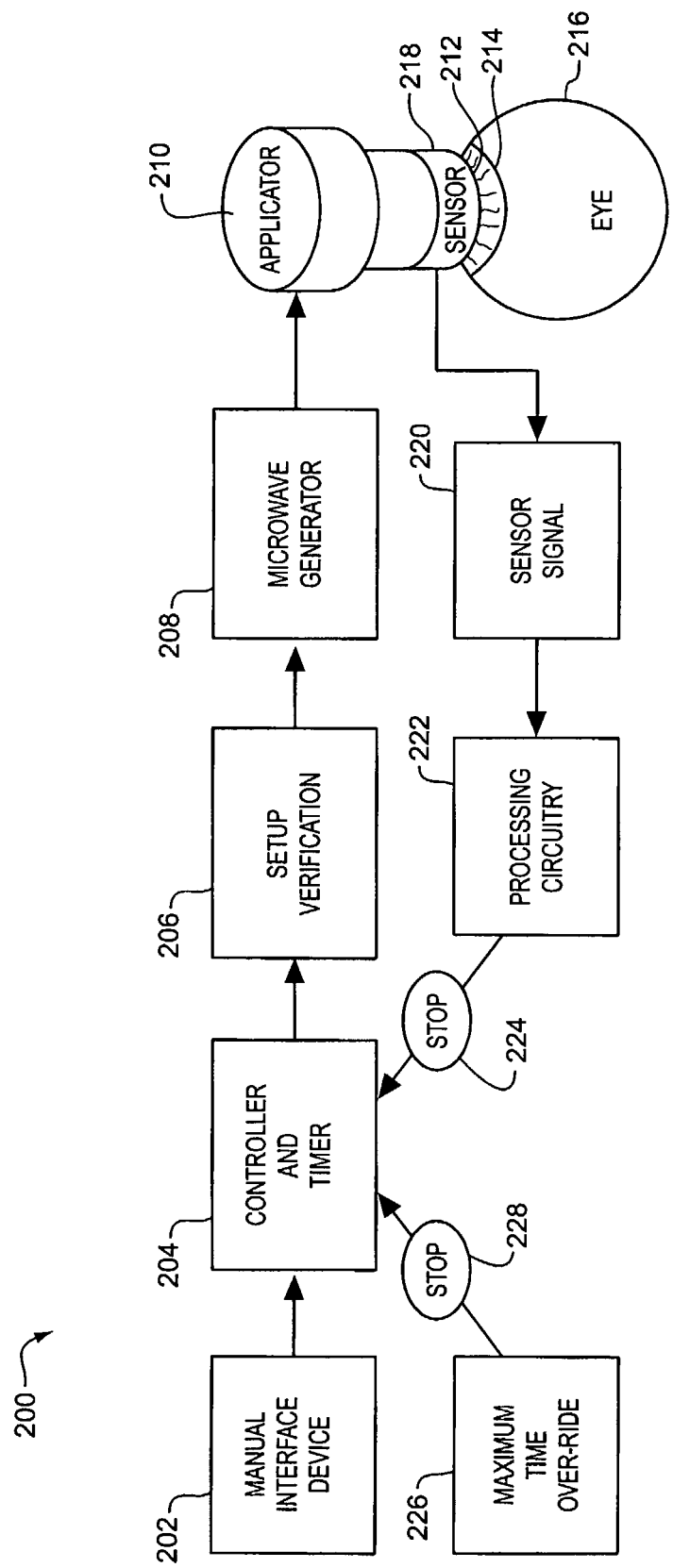
FIG. 2 is a block schematic diagram illustrating system components of a radio or microwave keratoplasty system in accordance with the principles described herein.

In FIG. 2, there will now be shown and described, by way of example and not by limitation, a thermokeratoplasty system 200 that operates by sensing a physical variable in an eye and providing sensed feedback affecting a vision correction modality. A physician or other medical worker manually accesses an interface device 202, such as a computer keyboard, that facilitates the selection and/or initiation of a treatment modality. The interface device 202 may request manual input, such as a predetermined amount of diopter correction that is required for a particular patient, baseline measurements of physical variables, astigmatism measurements, wavelength of microwave radiation, intensity of microwave radiation, selection of a treatment modality by specific selection or class of modality, and/or goals for adjusted physical variables obtainable as a result of treatment.

A programmable controller 204 accepts program instructions that optionally access user input data or program selections from the interface device 202 and causes system 200 to implement a selected vision correction modality. Setup verification in step 206 may be a user-interactive process that verifies the modality and assures that system 200 is correctly positioned or configured for thermokeratoplasty operations. Once setup is verified, a generator, such as microwave generator 208, produces energy that is useful for thermokeratoplasty purposes and supplies this energy, e.g., in the form of microwave energy, to an applicator 210. A near-microwave emission of 915 MHz (approved by the FCC for medical use) is preferred to reduce system cost; however, the microwave generator 208 may be operated at other any frequencies, such as 2450 MHz, that are conventionally used and understood to have therapeutic benefits according to a desired modality. In turn, applicator 210 produces corresponding near-field effects 212 in cornea 214 of eye 216.

The cornea 212 and eye 216 inherently have one or more variable physical properties (i.e., physical variables) that may be affected by the microwave or radiofrequency near-field effects 212 and the consequent temperature elevation. These physical variables may be measured by a sensor 218 to provide a sensor signal 220 that embodies a direct or indirect measurement of the physical variables. Processing circuitry 222 may receive the signal 220 and analyze the same to determine if and when the modality has achieved a desired effect that is relevant to the intended or planned outcome of the modality. Processing circuitry 222 may generate a stop signal 224 that terminates treatment when the physical variable has been modified to within a predetermined range or value. Sensor 218 for use with the applicator 210 may be one or more of the sensors described above, such as:

a thin film or microelectronic thermal transducer; or a mechanical transducer, such as a piezoresistive or piezoelectric device, or a force-sensitive quartz resonator that quantifies corneal elongation or internal pressure.

In one embodiment, a safety mechanism is built into program instructions for controller 204 as a clock-based maximum time override 226 that generates a stop signal 228 at the termination of a safe time interval for the selected modality. This feature may assure that operation of the microwave generator 206 does not exceed a specified amount of time at any given level of output and is intended to avoid thermal damage to the corneal epithelium, and especially the endothelium.

Figure 1:
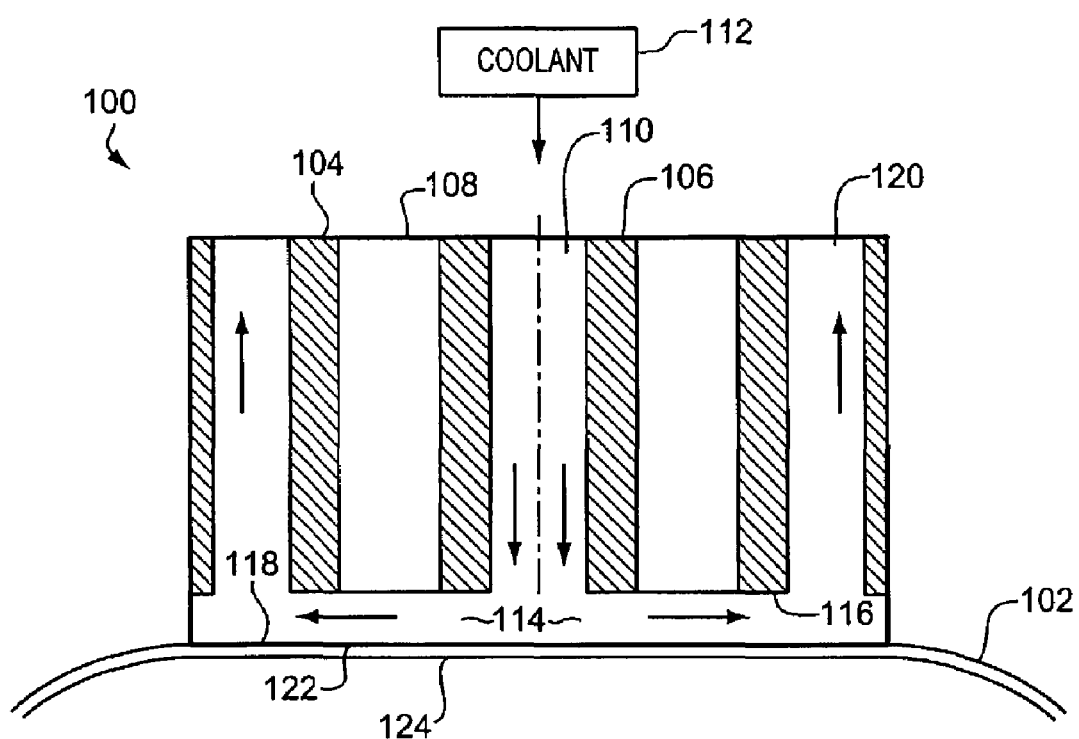
FIG. 1 shows a prior art microwave applicator.
Figure 3:
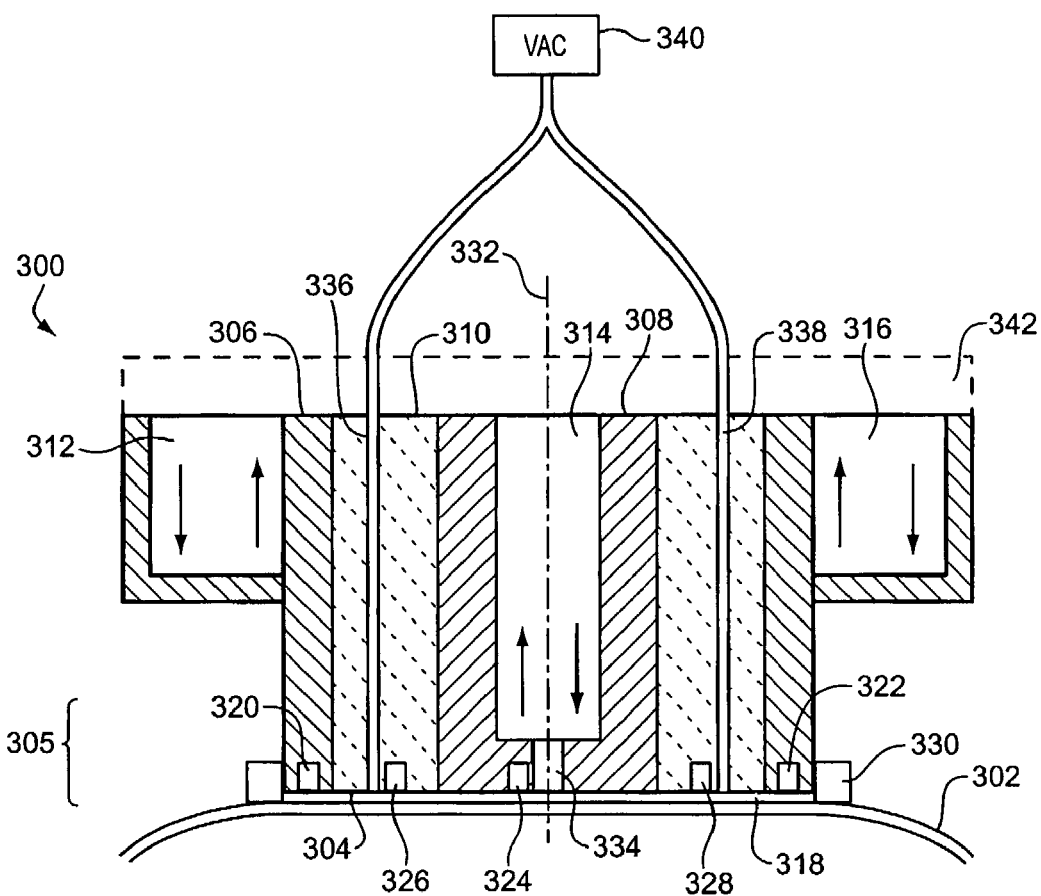
FIG. 3 is a side perspective midsectional view of one microwave applicator that is improved with respect to the prior art.

Most types of microwave thermokeratoplasty applicators 210 may be used generally in the aforementioned system 200, provided the applicator is fitted with the sensor 218. FIG. 3 depicts a side elevation midsectional view of a cylindrical applicator 300 that contains several improvements over the applicator 100 of FIG. 1. One such improvement is, for example, the absence of a flow gap between cornea 302 and a bottom surface 304 of applicator 300, such that no coolant circulates below applicator 300 or in the lower region 305, e.g., the bottom ten percent or so of applicator 300 proximate to cornea 302.

In one embodiment, an outer insulated microwave-conductive tube 306 circumscribes an inner insulated tube 308 that is also microwave conductive. Tubes 306 and 308 are concentric. A dielectric material 310 may separate tube 306 from tube 308. The spacing between tubes 306 and 308 controls penetration depth of microwave energy according to established microwave field theory. In one embodiment, chambers 312, 314, and 316, are configured for bidirectional coolant flow providing a predetermined amount of cooling from coolant (e.g., coolant 112, FIG. 1). Such flow is optionally regulated by controller 204 (see FIG. 2) to achieve a maximum temperature at mid-depth in cornea 302, for example, according to established thermal flux theory.

A bottom dielectric layer 318 may protect cornea 302 from deleterious temperature effects of electrical conduction current that, otherwise, would flow into cornea 302 from the tubes 306 and 308. The bottom dielectric layer 318 may separate bottom surface 304 from cornea 302. The dielectric layer 318 may be thin enough to minimize interference with microwave emissions and thick enough to prevent superficial deposition of electrical energy by flow of conduction current; superficial flow of a conduction current could interfere with the goal of achieving a mid-depth maximum temperature in cornea 302. By way of example, the dielectric layer 318 may be a biocompatible material, such as Teflon, deposited to a thickness of about 0.002 inches. Alternatively, the dielectric layer 318 may be a thermal conductor, such as hard-coat anodizing.

The sensor 218 (shown in FIG. 2) may be a type of sensor described above, and may, for example, comprise embedded microelectronic devices 320, 322 and/or 324 in the tubes 306 and 308, devices such as sensors 326 and/or 328 embedded in the dielectric material 310, or optional separate sensors such as sensor 330 deployed outside of applicator 300. Alternatively, the dielectric layer 318 is, for example, a grid of thin film transducers each operating as a wheatstone bridge. Where the applicator 300 is deployed with axis of symmetry 332 over a pupil, a transparent window 334 may be used to quantify the refractive effect of treatment with optical instrumentation, such as a videokeratoscope.

In one embodiment, vacuum passages 336 and 338 pass through the dielectric material 310, and connect to a vacuum source 340 for purposes of enhancing retention of applicator 300 in a fixed position relative to cornea 302 during treatment.

In alternative embodiments, a liquid coolant is not required. Chambers 312, 314, and 364 may be filled with a heat sink in thermal communication with an optional thermoelectric cooler device 342 that operates, for example, using a Peltier effect under the control of controller 204.

Figure 4:
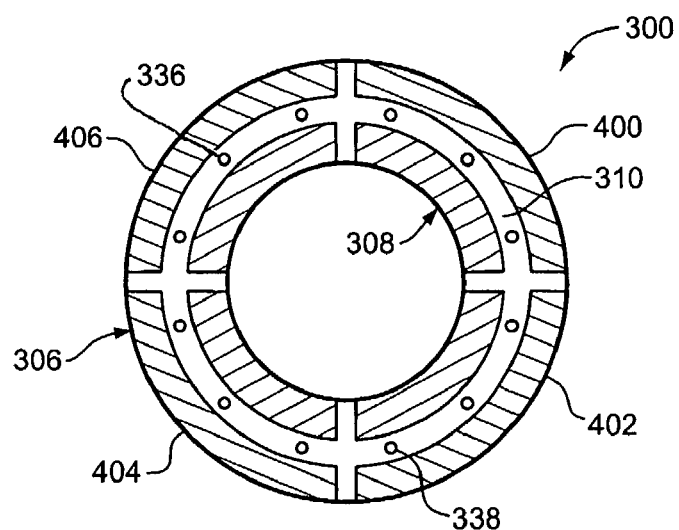
FIG. 4 is a top perspective midsectional view of the microwave applicator shown in FIG. 3.

FIG. 4 is a top midsectional view of applicator 300. Each of the tubes 306 and 308 may be divided into a plurality of discrete sectors or sections, which in FIG. 4 are quartile sections of coaxial extension, such as quartile sections 400, 402, 404, and 406 in the case of tube 306. Each of these sections 400-406 may be separately coupled with controller 204 (shown in FIG. 2) for individual operation where, for example, microwave radiation of different intensity, duty cycle, waveform, frequency, or duration may be applied to any one section, or the sections 400-406 may be driven wholly or partially in unison. There may be any number of sections separated by dielectric material 310 and any number of concentric tubes, such as tubes 306 and 308. The capability to drive discrete sections facilitates treatment of native astigmatism in the patient, and it offers further capacity not heretofore found, which is to provide modalites that are custom tailored to address a variety of diopter adjustments in optimized fashion by selectively providing more or less treatment energy to sections in a radially outboard pattern.

Figure 5:
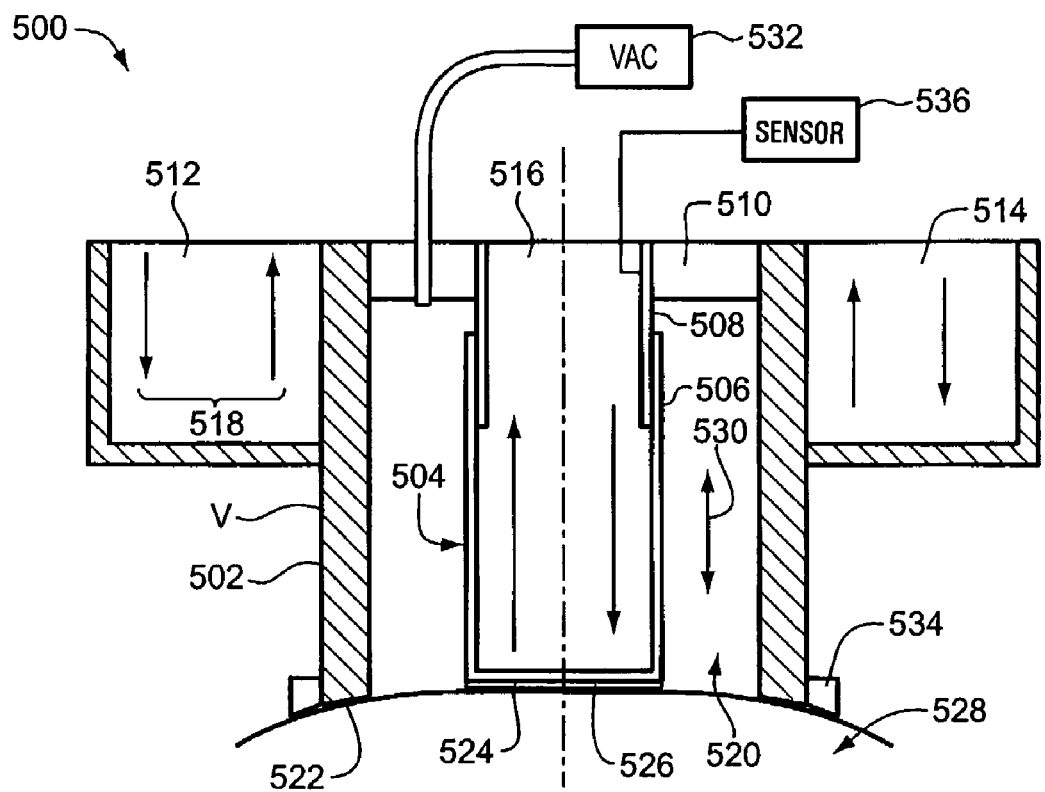
FIG. 5 is a side perspective midsectional view of one microwave thermokeratoplasty applicator that may be used in place of the applicator shown in FIG. 3.

FIG. 5 is a side elevation midsectional view of a cylindrical microwave or radiofrequency thermokeratoplasty applicator 500 that may be used in place of applicator 300. An outer insulated electrically-conductive tube 502 may circumscribe an inner telescoping insulated tube 504 that is also electrically-conductive. Inner tube 504 may be formed in at least two telescoping sections 506 and 508 that are in electrical contact with one another. The tubes 502 and 504 may be concentric. A dielectric material 510 may separate tube 502 from section 508. The spacing between tubes 502 and 504 controls penetration depth of microwave or radio-frequency energy according to established microwave and radio-frequency field theory. Generally, the near-field effects produce localized heating effects on corneal tissue without producing a radiation wave that is capable of heating the corneal endothelium to a point of damage. Chambers 512, 514, and 516 are configured for bidirectional coolant flow (e.g., as flow 518) generally as described with respect to applicator 300. An annular air gap 520 may surround the telescoping tube 504. Bottom surfaces 522 and 524 may be rounded to conform with an eye, e.g., generally to conform with a spherical shape established by ball-milling processes. For one embodiment, bottom surfaces 522 and 524 are coated with a material 526 that is both dielectric and heat conductive, such as Teflon powder coating material, or anodizing material. The material 526 may protect cornea 528 from deleterious temperature effects of electrical conduction current that, otherwise, would flow into cornea 528 from the tubes 502 and 504, according to principles described generally above with respect to applicator 300.

Section 504 may telescope axially over section 506, as shown by a double-headed arrow 530, to assure that material 526 is positioned in full contact with cornea 528. This sliding action may be facilitated by gravity or positive pressure exerted by coolant flowing in chamber 516. A vacuum pump 532 may also be used to exert a mild vacuum within chamber 516 to force this contact. Alternatively, a screw mechanism (not shown) may be positioned in air gap 520 to provide fixed and repeatable adjustments to the height of section 504.

Applicator 500 can include a sensor, e.g., sensor 218, which can, for example, include outside sensors 534 deployed outside of applicator 500 and/or embedded sensor devices not shown in FIG. 5. A second sensing device 536 may be used to sense whether full contact exists between the tubes 502, 504, and the cornea 528. Coroneal tissue contains relatively high amounts of water and is conductive. Thus, a voltage V applied to outer tube 502 may be sensed by the second sensing device 536 as a resistance or capacitance. The magnitude of resistance or capacitance may be correlated to the amount of contact between applicator 500 and cornea 528. A signal from the second sensor 536 may be used as part of the feedback system through processor circuitry 222 (FIG. 2) or may be operated independently of the feedback system and used solely as a means to assure contact between applicator 500 and cornea 528.

Since certain changes may be made in the above methods and systems without departing from the scope hereof, it is intended that all matter contained in the above description or shown in the accompanying drawing be interpreted as illustrative and not in a limiting sense. It is also to be understood that the following claims are to cover generic and specific features described herein, and all statements of the scope of the invention which, as a matter of language, might be said to fall there between.

I claim:

1. In a thermokeratoplasty system including an applicator for applying energy to a cornea to cause a thermally-induced pattern of shrinkage, the improvement comprising:
   a sensor configured to measure corneal surface temperature during a thermokeratoplasty operation and to provide a sensor signal representative of the corneal surface temperature; and
   a programmable controller adapted to provide control signals to the applicator to implement a desired vision correction result and further comprising a feedback system adapted to receive the sensor signal and analyze the sensor signal to determine when a treatment result has achieved an intended effect.

2. In the thermokeratoplasty system of claim 1, wherein the sensor is configured to measure the cornea temperature at depth.

3. In the thermokeratoplasty system of claim 1, wherein the feedback system operates by processing the sensor signal according to an empirical correlation that relates the sensor signal to a predetermined vision correction effect.

4. In the thermokeratoplasty system of claim 1, wherein the feedback system operates by processing the sensor signal to determine when the physical variable has been adjusted to achieve a predetermined quantity of the physical variable.

5. In the thermokeratoplasty system of claim 1, further comprising at least one additional sensor that provides an additional sensor signal, the feedback circuitry being configured to process the sensor signal and the additional sensor signal, in combination, to determine when the treatment modality has achieved the intended effect.

6. In the thermokeratoplasty system of claim 1, further comprising a microwave or radio-frequency applicator configured for direct contact with a cornea without a coolant flow gap between the applicator and the cornea.

7. In the thermokeratoplasty system of claim 6, further comprising the microwave or radio-frequency applicator including a plurality of discrete sectors.

8. In the thermokeratoplasty system of claim 7, wherein the plurality of discrete sectors are segmented portions of a tube that are selectively actuable for emission of electrical energy according to the treatment modality.

9. In the thermokeratoplasty system of claim 8, further comprising control circuitry for actuating the plurality of discrete sectors to emit electrical energy according to the treatment modality.

10. In the thermokeratoplasty system of claim 9, further comprising program instructions for the control circuitry providing a capability to change the actuation of one or more of the plurality of discrete sectors on the basis of the sensor signal.

11. In the thermokeratoplasty system of claim 9, the sensor comprising an array of sensors each allocated to a corresponding one of the plurality of discrete sensors and linked to the feedback system.

12. In the thermokeratoplasty system of claim 6, further comprising the applicator including at least one telescoping tubular member configured for positional adjustment of the telescoping tubular member relative to a cornea of the eye when the applicator is deployed for use in thermokeratoplasty operations.

13. In the thermokeratoplasty system of claim 6, further comprising means for sensing whether the applicator is engaged with a cornea of the eye when the applicator is deployed for use in thermokeratoplasty operations.

14. The system of claim 1, wherein the sensor is coupled to the applicator.

15. The system of claim 1, wherein the sensor signal representative of the corneal temperature includes information concerning an electrical voltage applied to a cornea.

16. The system of claim 1, wherein the sensor signal representative of the corneal temperature includes information selected from the group consisting of scalar, vector, and tensor temperature variables measured at the surface of a cornea.

17. The system of claim 1, wherein the sensor signal representative of the corneal temperature includes information selected from the group consisting of scalar, vector, and tensor temperature variables measured at depth in a cornea.

18. The system of claim 1, wherein the sensor signal representative of the corneal temperature includes information obtained from a thermal transducer.

19. The system of claim 18, wherein the sensor signal representative of the corneal temperature includes information selected from the group consisting of temperature and heat flux at the surface of a cornea.

20. The system of claim 18, wherein the sensor signal representative of the corneal temperature includes information selected from the group consisting of temperature and heat flux at a depth in a cornea.

21. The system of claim 18, wherein the thermal transducer is a type selected from the group consisting of a thermocouple, a thermistor, and a submillimeter-scale device.

22. In a thermokeratoplasty system including an applicator for applying energy to a cornea to cause a thermally-induced pattern of shrinkage, the improvement comprising:
   a sensor configured to measure corneal temperature as a corneal electrical property during a thermokeratoplasty operation and to provide a sensor signal representative of the corneal temperature; and
   a programmable controller adapted to provide control signals to the applicator to implement a desired vision correction result and further comprising a feedback system adapted to receive the sensor signal and analyze the sensor signal to determine when a treatment result has achieved an intended effect.

23. The system of claim 22, wherein the sensor is configured to measure the corneal electrical property as conductivity or permittivity.

* * * * *

UNITED STATES PATENT AND TRADEMARK OFFICE
CERTIFICATE OF CORRECTION

PATENT NO. : 7,377,917 B2  
APPLICATION NO. : 10/314670  
DATED : May 27, 2008  
INVENTOR(S) : B. Stuart Trembly Page 1 of 1

It is certified that error appears in the above-identified patent and that said Letters Patent is hereby corrected as shown below:

Column 4, line 12, "compliment" should read --complement--;

Signed and Sealed this

Twenty-first Day of October, 2008

JON W. DUDAS  
*Director of the United States Patent and Trademark Office*